United States Patent [19]

Gumaste et al.

[11] Patent Number: 5,693,016
[45] Date of Patent: Dec. 2, 1997

[54] SOLID STATE FLUID DELIVERY SYSTEM

[76] Inventors: Anand V. Gumaste, 7 Ardsley Ct., Robbinsville, N.J. 08691; Andrew L. Abrams, 26 Imperial Ave., Westport, Conn. 06880; Scott Fleming, 18 Riverview Dr., Ewing, N.J. 08628

[21] Appl. No.: 555,225

[22] Filed: Nov. 8, 1995

[51] Int. Cl.$^6$ .................................................. A61M 37/00
[52] U.S. Cl. ........................... 604/131; 604/151; 604/132
[58] Field of Search .......................... 417/412, 413.2, 417/413.1, 474; 604/68, 892.1, 131, 132, 151, 153

[56] References Cited

U.S. PATENT DOCUMENTS

| | | | |
|---|---|---|---|
| 4,449,893 | 5/1984 | Beckman | 417/412 |
| 4,787,888 | 11/1988 | Fox . | |
| 5,007,438 | 4/1991 | Tachibana et al. . | |
| 5,094,594 | 3/1992 | Brennan . | |
| 5,415,629 | 5/1995 | Henley . | |

FOREIGN PATENT DOCUMENTS

| | | | |
|---|---|---|---|
| 6147104 | 5/1994 | Japan | 417/413.2 |
| 2238833 | 6/1991 | United Kingdom | 417/413.2 |

*Primary Examiner*—Sam Rimell
*Assistant Examiner*—Luke Yeh
*Attorney, Agent, or Firm*—Hayes, Soloway, Hennessey, Grossman & Hage, P.C.

[57] ABSTRACT

An apparatus and method are disclosed that utilize piezo-electric materials as part of a delivery system capable of the rapidly repetitive dispensing of a fluid to an intended target site. In a particular embodiment, the apparatus contemplates a needleless injection system which comprises a second housing structure, a plurality of piezoelectric elements which are stacked in a layered fashion within the second housing structure, electronic circuitry disposed proximate the second housing structure and hence the layered stack of piezoelectric elements, and a first housing structure containing a fluid reservoir operatively connected to the second housing structure so as to allow fluid contained with the fluid reservoir to communicate with the layered stack of piezoelectric elements. The layered stack of piezoelectric elements has at least one common aperture formed therein which extends therethrough.

18 Claims, 3 Drawing Sheets

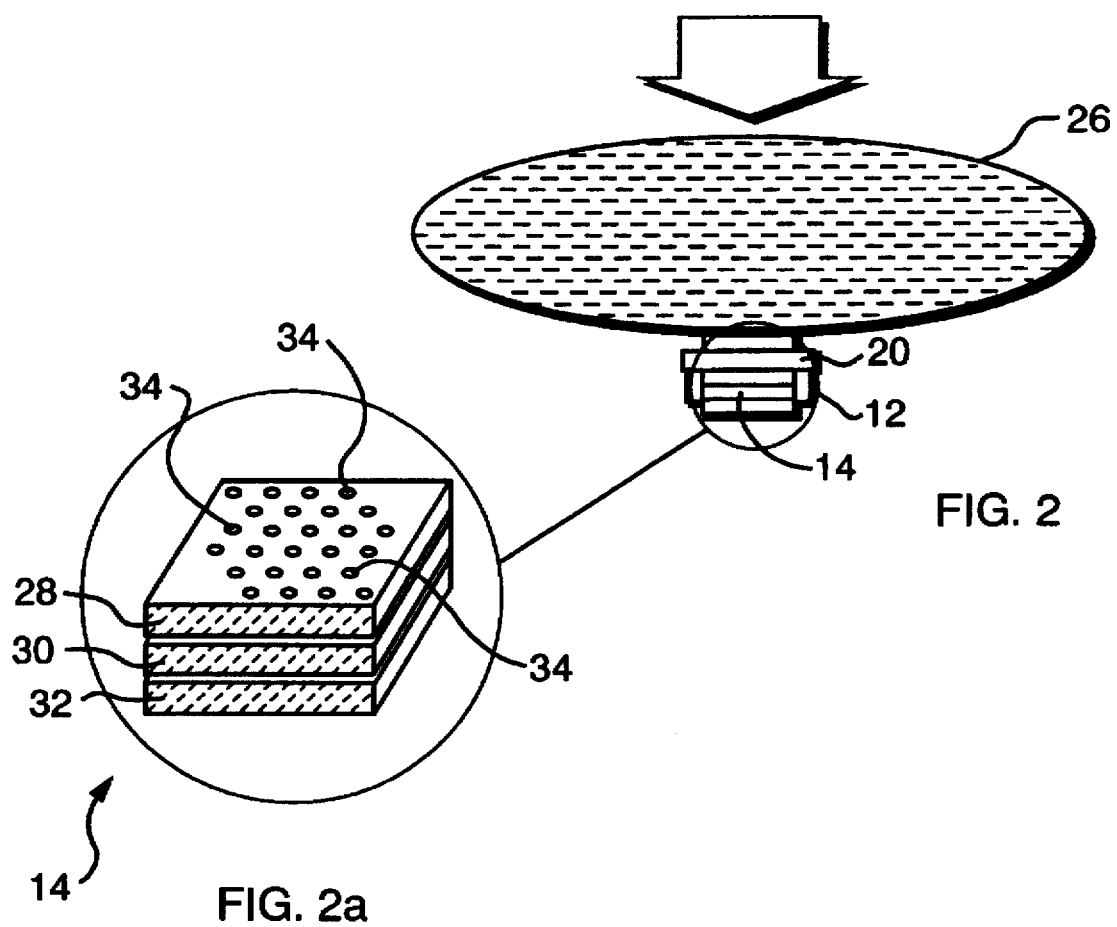

SOLID STATE FLUID DELIVERY SYSTEM

FIELD OF THE INVENTION

The present invention relates generally to fluid delivery systems and, more particularly, to solid state delivery systems that do not require a needle-like nozzle and that utilize piezoelectric materials to achieve the rapid injection of accurate small quantities of fluid.

BACKGROUND OF THE INVENTION

The delivery of fluids, including within the definition of this term liquids, solid particles and gases, in a variety of contexts has progressed in recent years to embrace various automated transport and delivery systems. Specifically, the development of equipment requiring rapid delivery of microquantities of fluid to a particular location or target, finds its application to such diverse areas as, for example, fuel delivery for internal combustion and turbine-type engines, the delivery of reagents in chemical and biological research and diagnostic procedures, and the delivery of microquantities of medicaments to patents for therapeutic purposes. In all of these instances, the extant technology and equipment is limited in its ability to define and control parameters for the precise delivery of exceedingly small volumes of liquid in rapid repeatable fashion. The problems and corresponding needs for improved equipment are particularly acute in the area of medicament delivery, as described in greater detail below.

Medications are injected through the skin to provide therapeutic effects which are more efficient or unobtainable through other drug delivery routes. Some reasons for injecting medications are: 1.) chemical destruction of the medication by the gastrointestinal tract; 2.) poor absorption; 3.) patient too sick or too young to take the medicine orally; and 4.) need for rapid action of the drug.

The most commonly used device to inject a medication is a hypodermic needle attached to a plunger syringe. These syringes come in a variety of sizes and can be automated by connecting them to a pump mechanism, or a pump designed for injection can be utilized. Such pumps are used primarily for intravascular or intrathecal delivery.

A number of needleless injection systems presently exist. These systems use a compressed gas, either $CO_2$ or compressed air. The gas is released at high pressure on demand and acts on a movable piston which forces medication out of the nozzle of the syringe. The resulting high velocity jet stream deposits the medication under the skin of a patient. All needleless injection systems have the advantage of not requiring "sharps" which are considered a bio-hazard and require careful disposal.

Present needleless injection systems are generally large and noisy. They require either the cocking of a spring mechanism or an attachment to a $CO_2$ source. Use of these devices requires a trained, skilled operator. Also, they must be disassembled to be cleaned. Furthermore, they cannot be programmed for automated delivery.

Certain devices that assist in the administration of medication and which utilize piezoelectric materials for performing certain administration functions have been described. For example, U.S. Pat. No. 4,787,888 to Fox, U.S. Pat. No. 5,094,594 to Brennan, U.S. Pat. No. 5,415,629 to Henley, and U.S. Pat. No. 5,007,438 to Tachibana et al. are all directed toward the administration of medications and/or the use of piezoelectric materials for such administration or otherwise.

More particularly, U.S. Pat. No. 4,787,888 to Fox discloses a bandage assembly for percutaneous administration of medication wherein a piezoelectric material is utilized so as to generate sonic vibrations for assisting the medication to be absorbed through the skin of a patient. It should be noted that this patent fails to disclose the use of piezoelectric materials as injection means wherein medication is forcibly introduced through the skin of a patient.

U.S. Pat. No. 5,094,594 to Brennan discloses a piezoelectric pumping device wherein piezoelectric material is utilized as a pumping means in conjunction with an electrophoretic unit. The Brennan apparatus is complex and cumbersome, and lacks the applicability to a needleless medicament injection system, and particularly such a system as is capable of forcibly introducing medication through the skin of a patient.

U.S. Pat. No. 5,415,629 to Henley discloses a programmable apparatus for the transdermal delivery of medication wherein piezoelectric elements are utilized for providing ultrasonic vibrations which enhance penetration of the medication through the skin of a patient. It should be noted that this patent fails to disclose the use of piezoelectric materials as injection means wherein medication is forcibly introduced through the skin of a patient.

U.S. Pat. No. 5,007,438 to Tachibana et al. disclose an endermic application kit for external medicines wherein an ultrasonic oscillation is utilized to enhance the absorption of medication by the skin of a patient. It should be noted that this patent fails to disclose the use of piezoelectric materials as injection means wherein medication is forcibly introduced through the skin of a patient. In fact, this patent fails to disclose the use of piezoelectric materials in any manner.

Although the above-mentioned patents are generally directed toward the metered delivery of fluids, including in some instances, medications, and illustrate prior applications of piezoelectric materials for their specific objectives, none are directed toward providing a method for utilizing piezoelectric materials as injection means wherein medication is forcibly introduced through the skin of a patient. Such a method would realize all of the benefits of a needleless injection system along with many other advantages as detailed below.

More generally, the development of a simple and inexpensive delivery system that can transfer small amounts of fluid on a rapid, quiet, and repeatable basis would be highly valued not only in regard to the injection of medicaments, but in the other commercial and industrial areas listed above where similar needs exist. Accordingly, it is toward the fulfillment of the needs expressed above that the present invention is directed.

SUMMARY OF THE INVENTION

In its broadest aspect the present invention extends to an apparatus and corresponding method for the rapid delivery of a fluid. The apparatus of the invention comprises a fluid storing component comprising a first housing having walls defining a dispensing chamber of adjustable size for containing the fluid to be dispensed, at least one nozzle element defined in at least one of said walls for the discharge therethrough of said fluid, and a second housing which, in one embodiment, may be adapted for detachable association to said first housing, including pump means for receiving and forcing a predetermined volume of said fluid out of said apparatus and toward said target. The pump means comprises a plurality of piezoelectric elements adapted in a preferred embodiment to reside in a stacked relationship, and adapted for sequential excitation to simulate a peristaltic motion, to receive a predetermined quantity of the fluid to be dispensed and thereafter to eject the fluid toward the intended target.

The invention also extends to a method for utilizing piezoelectric materials as a pump means as described above, wherein the sequential excitation of the piezoelectric elements forces the fluid to egress the dispensing chamber and delivers the fluid to its intended target. More particularly, the method comprises the sequential excitation of plural piezoelectric elements disposed in stacked adjacent relationship, first to define a chamber that receives a predetermined volume of the fluid, and thereafter, to eject the fluid from the chamber by the rapid reduction in chamber volume. The application of this sequential arrangement facilitates both speed and accuracy, as precise metering and rapidly repeatable delivery are enabled.

The present invention broadly covers the fabrication of layered piezoelectric materials and their sequential excitation to function as a "peristaltic-like" pump, to rhythmically draw forward and segregate a predetermined volume of fluid, and thereafter expel said fluid, wherein each of these steps can occur in rapid and continuous sequence, to deliver precise and equal volumes of the fluid at a high rate of frequency for an extended period of time, likewise within the control of the operator.

A particularly advantageous application of the inventive pump construction and apparatus is found in its use as an needleless injection means for the delivery of a fluid medication as by forcible introduction through the skin of a patient. The pump means may therefore comprise at least two piezoelectric elements disposed in stacked arrangement, with at least one opening journaled through adjacent layers. The size of the opening may be adjusted in use in response to excitation or relaxation of the piezoelectric element or elements. It can thereby be appreciated that the sequential excitation of the piezoelectric elements as described herein, can first define a chamber for the reception of a quantity of the fluid to be dispensed, and can thereafter contract the defined volume of such chamber to eject the fluid toward the intended target.

An actuator for the excitation of the piezoelectric elements is included, which may include means for controlling the amount and temporal schedule for dispensing of said fluid. For example, the actuator of the invention may include a battery unit for portable application of the apparatus, and circuitry including a programmable controller for pre-setting the amount, frequency and duration of fluid dispensing. This capability has particular value in the instance where the inventive apparatus is applied to the administration of medication, whether in a clinical setting or in a constant and personal setting.

In a preferred embodiment, the invention comprises an apparatus for the rapid and accurate delivery of medical reagents and medicaments, and particularly extends to a needleless injection system which is capable of forcibly delivering medication transdermally to a patient. A particular apparatus comprises a needleless injection system comprising a fluid container component comprising a first housing defining a dispensing chamber and including at least one nozzle element, and a second fluid dispensing component comprising a plurality of piezoelectric elements which are stacked in a layered fashion within the housing, and an actuator means including electronic circuitry and in the instance of a portable unit, a battery, which may be disposed proximate to the piezoelectric elements. More particularly, the first housing may comprise a fluid reservoir operatively connected to the second housing so as to interface with the layered stack of piezoelectric elements. The above-stated components may be modular in construction, to allow for the repeated use of the fluid dispensing component containing the piezoelectric elements and the electronic circuitry, and the disposal of the first housing or fluid container component. The first and second housings would accordingly be detachably attached to each other and may, as a unit, be releasably affixed to a surface that is to receive the fluid to be dispensed, as in the instance of the removable attachment to a patient.

As stated above, the layered stack of piezoelectric elements has at least one common aperture formed therein which extends therethrough. Each aperture may be opened and closed in each piezoelectric element relative to the degree of excitation applied, by the electronic circuitry, to each piezoelectric element. Thus, the size of each aperture in each piezoelectric element may be individually controlled by the electronic circuitry so as to allow fluid medication from the fluid reservoir to be either present or absent from the aperture area. Consequently, the layered stack of piezoelectric elements may be utilized as a pump wherein fluid medication from the fluid reservoir is forced in to and out from each aperture in each piezoelectric element in the layered stack and then forcibly introduced through the skin of a patient. During this pump action, the apertures act as sealed dispensing chambers where fluid medication is temporarily stored as it flows through the layered stack of piezoelectric elements.

The apparatus of the present invention may be constructed as a portable unit with battery operation, in the instance where it is used for the delivery of medication to an ambulatory individual. Further, the housing including the fluid container may be fabricated either as an integral unit with the fluid dispensing component unit that may be discarded in its entirety, or as a modular construction wherein it is adapted to be detached from the second fluid dispensing component either for refilling or disposal.

The use of piezoelectric actuation to mechanically force the discrete volume of fluid rapidly and at high pressure, together with the simplified construction of the apparatus makes the manufacture and use of the present apparatus particularly attractive, and further augments the advantages thereof. For example, medications dispensed with the present apparatus may be delivered in small doses within short time intervals, and may thereby provide a more precise administration of a medication.

Accordingly, a principal object of the present invention is to provide a method and apparatus for the rapid and efficient delivery of fluids to target destinations, that are simple and economical to manufacture and use.

It is a further object of the present invention to provide an apparatus as aforesaid, that utilizes piezoelectric materials as a pump or injection means capable of forcibly delivering the fluid to the target destination.

It is a still further object of the present invention to provide an injection system that utilizes the properties of piezoelectric materials to respond rapidly to applied potentials, and to apply them as valves and powerful pumps and to assemble them as a unit.

Another object of the present invention is to provide a needleless, quiet, compact, inexpensive, easy to use, battery operated injection system, that is useful for the delivery of medication to a patient.

Another object of the present invention is to reduce medication delivery pain by many small low volume injections.

Another object of the present invention is to reduce the skill required by an operator of an injection system, and allow self medication injection, or medication injection by persons not specially trained.

Another object of the present invention is to provide an injection system which would allow medications which are given orally, rectally, or by other means for convenient home delivery to be delivered comfortably, and to provide all the benefits of transcutaneous drug delivery.

Another object of the present invention is to have programmability, and the possibility of continuous, or predetermined interval, medication delivery by an attached system.

Other objects and advantages of the present invention will become apparent to those skilled in the art from a review of the following detailed description and claims, in conjunction with the accompanying drawings which are appended hereto.

BRIEF DESCRIPTION OF THE DRAWINGS

In order to facilitate a fuller understanding of the present invention, reference is now made to the appended drawings. The drawings should not be construed as limiting the present invention, but are intended to be exemplary only.

FIG. 2 is a cross sectional view of some of the components of the needleless injection system shown in FIG. 1 along with another type of fluid reservoir and FIG. 2a is a detailed view of the layered stack of piezoelectric elements.

DETAILED DESCRIPTION OF THE PRESENT INVENTION

In its broadest aspect, the present invention relates to a delivery system for fluids, including powders, liquids and gases, that is capable of rapidly repetitive discharge of a precise and minute amount of such fluid on a continuous basis. Such a system finds particular application in a variety of contemporary industrial settings, extending from machinery design and operation, to medical devices for the administration of reagents and medications.

Accordingly, the apparatus of the invention comprises: at least one first housing having walls defining a dispensing chamber of adjustable volume for said fluid, and at least one nozzle element defined in one of said walls for the discharge of said fluid; at least one second housing which may be adapted, in one embodiment, for detachable association with said first housing, including pump means comprising at least one piezoelectric element for forcing a predetermined quantity of said fluid out of said dispensing chamber and through said at least one nozzle element; and actuation means including controller means for exciting said pump means to force said fluid out of said dispensing chamber, and for controlling the operation of said pump means.

A particular embodiment of the contemplated apparatus is illustrated herein in relation to an apparatus for the needleless delivery of medication, and the following description is presented in detailed exposition of that application and embodiment. It is to be understood, however, that the features and principles of the invention extend beyond the following nonlimiting illustration.

Figure 1:
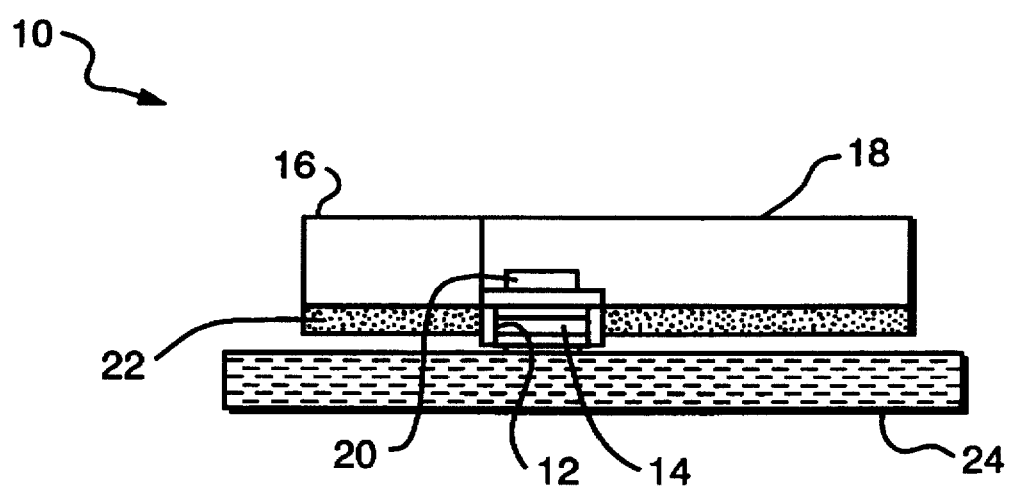
FIG. 1 is a cross sectional view of a needleless injection system according to the present invention.

Referring to the figures wherein like numerals designate like parts, and particularly to FIG. 1, there is shown a solid state needleless injection system 10 according to the present invention that utilizes piezoelectric materials so as to provide a force that is capable of injecting matter contained within a sealed dispensing chamber through the skin of a patient. The needleless injection system 10 comprises a second housing structure 12, plural piezoelectric elements 14 (three illustrated herein) stacked in a layered fashion within second housing structure 12, electronic circuitry 16 disposed proximate second housing structure 12 and hence the layered stack of piezoelectric elements 14; and a first housing structure comprising a fluid reservoir 18, disposed proximate to second housing structure 12 and operatively connected thereto so as to allow fluid medication contained with the fluid reservoir 18 to communicate with the layered stack of piezoelectric elements 14. The interface 20 between the fluid reservoir 18 and the second housing structure 12 as illustrated, may comprise a luer-lock connector which allows for quick and easy attachment and removal of the fluid reservoir 18 from housing structure 12. While the preceding description relates to the use of a modular design where the fluid reservoir 18 and the second housing structure 12 are separable, the economies of manufacturing cost allow for the fabrication of the present apparatus as a single unit that, for example, may be disposable in its entirety. Accordingly, the present invention is intended to cover this variation within its scope.

It should be noted that the electronic circuitry 16 is provided and distributed so as to allow the piezoelectric elements 14 to be individually excited, typically with a steady state DC voltage. It should also be noted that although the use of three piezoelectric elements 14 is illustrated, the apparatus could be operated with as few as two such elements 14. Conversely, multiple units exceeding those referenced or illustrated are contemplated within the scope hereof.

Referring further to FIG. 1, an adhesive base 22 may be provided upon which the second housing structure including the electronic circuitry 16 and the fluid reservoir 18, and through which the first housing structure 12 and hence the layered stack of piezoelectric elements 14 are mounted. The adhesive base 22 allows the entire needleless injection system 10 to be easily removably attached to vicinity of the target for the dispensing of fluid, such as the skin 24 of a patient illustrated herein. In the illustrated instance, the system 10 is constructed and applied in similar fashion to a bandage or a patch.

Referring to FIG. 2, the second housing structure 12 and the layered stack of piezoelectric elements 14 are shown connected, through interface 20, to another type of fluid reservoir 26. This type of fluid reservoir 26 requires external pressure to be applied thereto so as to force fluid medication therefrom, as compared to the fluid reservoir 18 described above which may have electronically actuated means for forcing fluid medication therefrom. Naturally, the fluid reservoirs illustrated herein are presented for purposes of illustration and not limitation, as the invention contemplates the use of reservoirs having various adaptations and means for the discharge or release of contained fluid.

Also shown in FIG. 2a is a detailed view of the layered stack of piezoelectric elements 14. From this view, it can be seen that the layered stack of piezoelectric elements 14 as illustrated comprises an upper piezoelectric element 28, a middle piezoelectric element 30, and a lower piezoelectric element 32. As discussed earlier herein, the invention contemplates the inclusion of only two piezoelectric elements, in which event, for example, only upper element 28 and middle element 30 would be present, and would operate as described later on herein. The invention is thereby contemplated to embrace this further embodiment within its scope.

Referring further to FIG. 2a, piezoelectric elements 28, 30 and 32 as illustrated are secured to each other with an adhesive (not shown). Of course, elements 28 may clamp together, and the invention is not limited to a particular method of securement. Should an adhesive be used, such adhesive may be of a type that will not allow fluid medication to seep therethrough. Also, it should be noted that such an adhesive should desirably be pliable so as to allow the individual piezoelectric elements 28, 30 and 32 to move relative to one another, as will be described in detail below. Further, although the layered stack of piezoelectric elements 14 is shown to be rectangular in shape, stack 14 may be formed in a variety of shapes such as, for example, as a cylinder. Likewise, the shape of the layered stack of piezoelectric elements 14 and the shape of the rigid housing structure 12 may correspond so as to ensure efficient and compact construction of this component of the system 10.

A plurality of common apertures 34 are formed in the layered stack of piezoelectric elements 14. The apertures 34 are termed common because they are aligned and extend down through the entire layered stack of piezoelectric elements 14. The diameter of each of the apertures 34 may vary, and, for example, may be as small as 50 micrometers. In such last-mentioned instance, the apertures 34 may be preferably formed using a laser.

Figure 3:
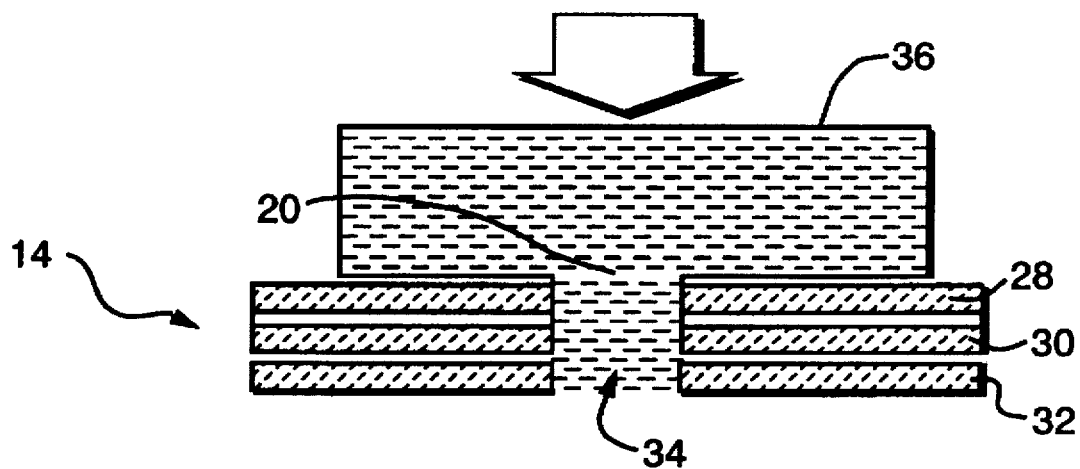
FIG. 3 is a close-up cross sectional view of a common aperture in the layered stack of piezoelectric elements according to the present invention, along with a functional representation of a fluid reservoir.

Referring to FIG. 3, the layered stack of piezoelectric elements 14 is shown with a common aperture 34, along with a functional representation of a fluid reservoir 36 an interface 20. In this particular view, all of the piezoelectric elements 28, 30 and 32 are in a dormant state (i.e. not excited). Thus, the common aperture 34 has a constant diameter extending all the way through the layered stack of piezoelectric elements 14.

Figure 4A:
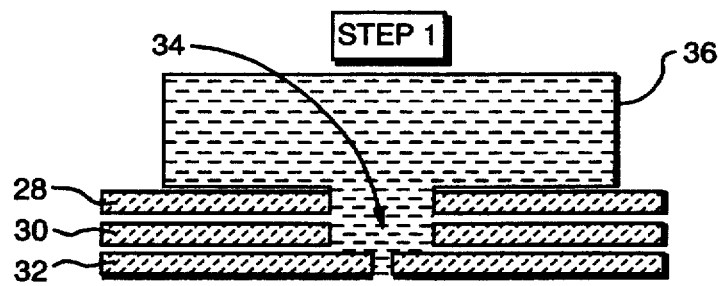
FIGS. 4a–4d are enlarged cross sectional views showing the sequence of operation of a needleless injection system according to the present invention.

Referring to FIG. 4a, the lower piezoelectric element 32 is excited so as to narrow its section of the common aperture 34 to about 25 microns in diameter. This step allows fluid medication to enter into the aperture 34 adjacent the upper piezoelectric element 28 and the middle piezoelectric element 30. In the instance where lower piezoelectric element 32 is absent, the aperture 34 could be provided with a constricted orifice or nozzle element that would effectively curtail appreciable fluid escape and thereby confer an equivalent function and effect to that of piezoelectric element 32.

Figure 4B:
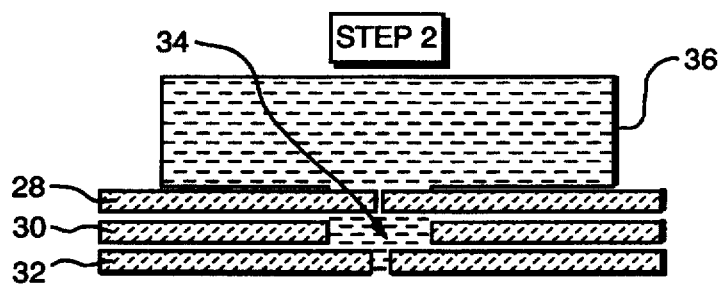

Referring to FIG. 4b, the upper piezoelectric element 28 is excited so as to narrow its section of the common aperture 34. This step essentially creates a sealed dispensing chamber in the aperture 34 adjacent the middle piezoelectric element 30.

Figure 4C:
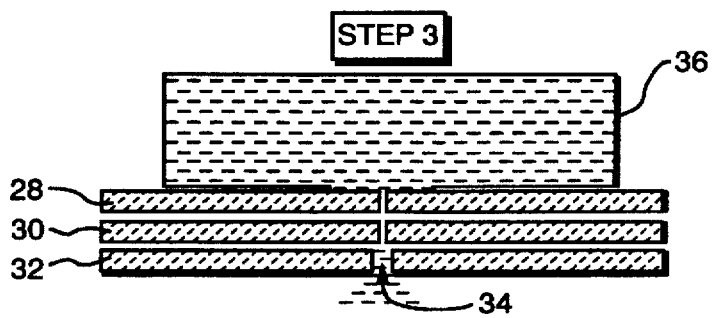

Referring to FIG. 4c, the middle piezoelectric element 30 is excited so as to narrow its section of the common aperture 34. This step forces the fluid medication out of the sealed dispensing chamber (i.e. the section of the common aperture 34 adjacent the middle piezoelectric element 30) and through the aperture opening in the lower piezoelectric element 32. Since, in application, the lower piezoelectric element 32 will be directly abutting the skin of a patient, the fluid medication will be forcibly introduced through the skin of the patient.

Figure 4D:
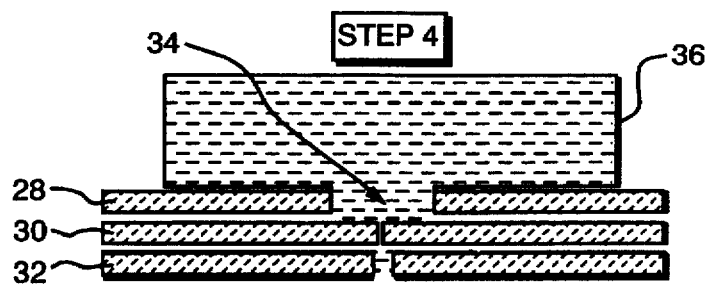

Referring to FIG. 4d, the upper piezoelectric element 28 is relaxed so as to expand its section of the common aperture 34 and thereby allow the entire sequential process to be repeated. Indeed, this process can be repeated until all of the fluid medication is dispensed from a fluid reservoir 18, 26. This entire sequential process can probably best be described as a peristaltic pumping action.

First housing structure 12 may be fabricated of a variety of materials, such as plastic or metal, and second housing structure including fluid reservoir 18, 26 may be fabricated of a variety of materials, such as plastic or a collapsible material. Also, fluid reservoir 18, 26 may take many different forms as indicated in FIGS. 1 and 2. Further, piezoelectric elements such as illustrative elements 28, 30 and 32 may be fabricated from a variety of piezoelectric materials, such as lead-zirconate/lead titanate (PZT).

Finally, it should be noted that throughout all of the above-described embodiments electrical connections must be made between the electronic circuitry 16 and the individual piezoelectric elements 28, 30 and 32. This is typically accomplished by providing each of the piezoelectric elements 28, 30 and 32 with electrodes (not shown) and electrically connecting these electrodes to the electronic circuitry 16. The electronic circuitry 16 may be somewhat sophisticated so as to allow programmability, with the possibility of continuous, or predetermined interval, delivery of the fluid medication.

Thus, the fluid medication is forced out of the dispensing chamber 20 through the injection port 28 at a pressure sufficient enough to penetrate the skin of a patient. This cycle can be repeated at various rates, and an illustrative, non-limiting range of repetition of from about 100 to about 2000 Hz range may be used.

As previously mentioned, more than one injection port 28 can be provided in the dispensing chamber 20, and hence in the second housing structure 18. Such would allow for a more widespread injection area which would reduce discomfort and irritation at an injection site. An illustrative and non-limiting size for an injection port 28 may be about 0.001 inches in diameter.

Throughout all of the above-described embodiments, an external electrical excitation (not shown) is required for the piezoelectric elements 28, 30 and 32. Such external electrical excitation typically comprises a DC voltage source having electrodes which are attached to the piezoelectric materials and to the coil, respectively.

With the present invention method now fully described, it can thus be seen that the primary objective set forth above is efficiently attained and, since certain changes may be made in the above-described embodiments without departing from the scope of the invention, it is intended that all matter contained in the above description or shown in the accompanying drawings shall be interpreted as illustrative and not restrictive, the scope of the invention being defined in the appended claims.

What is claimed is:

1. An apparatus for the rapid and repeatable delivery of small quantities of a fluid to an intended target, comprising:
   A. at least one first housing having walls defining a dispensing chamber for said fluid, and at least one nozzle element defined in one of said walls for the discharge of said fluid; and
   B. at least one second housing communicating with said first housing, said second housing comprising pump means comprising a plurality of piezoelectric elements disposed in a stacked arrangement adjacent one another, each of said piezoelectric elements having at least one opening therein, said openings being journaled within each of said piezoelectric elements in axial alignment as between adjacent said piezoelectric elements, said axially aligned stacked piezoelectric elements being pliably sealed to one another whereby to define a non-porous chamber for receiving and holding a predetermined volume of said fluid, said plurality of piezoelectric elements being adapted for sequential excitation to simulate a peristaltic motion whereby to receive a predetermined volume of said fluid from said dispensing chamber, and thereafter to eject the same through said at least one nozzle element toward said target; and actuation means for exciting said pump means.

2. The apparatus according to claim 1, wherein said plurality of piezoelectric elements comprise at least two piezoelectric elements stacked adjacent each other.

3. The apparatus according to claim 1, wherein said plurality of piezoelectric elements comprise three piezoelectric elements stacked adjacent each other.

4. The apparatus according to claim 1, wherein said first housing and said second housing are integral with each other, and may be disposable as a unit.

5. The apparatus according to claim 1, wherein said first housing is disposable.

6. The apparatus according to claim 1, wherein said apparatus is portable and said actuation means comprises a battery.

7. The apparatus according to claim 1, wherein plural nozzle elements are defined.

8. The apparatus according to claim 1, wherein plural openings are defined in each of said piezoelectric elements.

9. A needleless injection system that utilizes layered piezoelectric materials to forcibly introducing fluid medication through the skin of a patient, said system comprising:

a second housing having a first opening and a second opening formed the therein, a plurality of piezoelectric elements, said plurality of piezoelectric elements being stacked in a layered fashion and pliably sealed to one another within said second housing between said first opening and said second opening, each of said plurality of piezoelectric elements having an aperture formed therein, each said aperture being aligned so as to form a common aperture extending through said layered stack of piezoelectric elements from said first opening to said second opening whereby to define a chamber for receiving and holding a predetermined volume of said fluid;

a first housing comprising a fluid reservoir, said fluid reservoir being operatively connected to said first opening of said second housing so as to allow fluid medication contained within said fluid reservoir to communicate with said layered stack of piezoelectric elements; and electronic circuitry, said electronic circuitry being electrically connected to said layered stack of piezoelectric elements so as to allow each of said plurality of piezoelectric elements to be individually excited and the size of each of said aperture to be individually controlled, thereby allowing said layered stack of piezoelectric elements to be utilized as a pump wherein fluid medication from said fluid reservoir may be forced into and out from each said aperture and ultimately be forcibly introduced through the skin of a patient.

10. The system according to claim 9, wherein said second housing, said first housing and said electronic circuitry are integral with each other.

11. The system according to claim 9, further comprising an interface connector between said fluid reservoir and said first opening of said second housing.

12. The system according to claim 10, wherein said interface connector comprises a luer-lock connector so as to allow quick and easy attachment and removal of said fluid reservoir from said second housing.

13. The system according to claim 9, further comprising securement means upon which said electronic circuitry and said fluid reservoir and through which said second housing and hence said layered stack of piezoelectric elements are mounted so as to allow said system to be easily removably attached to a patient.

14. The system according to claim 9, wherein said plurality of piezoelectric elements comprise at least two piezoelectric elements stacked in a layered fashion within said second housing between said first opening and said second opening.

15. The system according to claim 9, wherein each of said plurality of piezoelectric elements have a plurality of apertures formed therein, wherein each of said plurality apertures are aligned in groups so as to form a plurality of common apertures extending through said layered stack of piezoelectric elements from said first opening to said second opening.

16. The system according to claim 9, wherein said fluid reservoir includes electronically actuated means for forcing fluid medication therefrom.

17. The system according to claim 9, wherein said fluid reservoir may be fabricated of a collapsible material so as to allow fluid medication to be forced therefrom by external pressure.

18. A needleless injection method that utilizes layered piezoelectric materials to forcibly introduce fluid medication through the skin of a patient, said method comprising the steps of:

providing a second housing, having a first opening and a second opening formed therein;

stacking a plurality of piezoelectric elements in a layered fashion within said second housing between said first opening and said second opening, each of said plurality of piezoelectric elements being pliably sealed to one another, and each having an aperture formed therein, each said aperture being aligned so as to form a chamber for receiving and holding a predetermined volume of said fluid, extending through said layered stack of piezoelectric elements from said first opening to said second opening;

operatively connecting a first housing containing a fluid reservoir to said first opening of said second housing so as to allow fluid medication contained within said fluid reservoir to communicate with said layered stack of piezoelectric elements; and individually exciting each of said plurality of piezoelectric elements so as to allow the size of each said aperture to be individually controlled, thereby allowing said layered stack of piezoelectric elements to be utilized as a pump wherein fluid medication from said fluid reservoir may be forced into and out from each said aperture and ultimately be forcibly introduced through the skin of a patient.

* * * * *